United States Patent
Johs et al.

(10) Patent No.: US 7,301,631 B1
(45) Date of Patent: Nov. 27, 2007

(54) CONTROL OF UNCERTAIN ANGLE OF INCIDENCE OF BEAM FROM ARC LAMP

(75) Inventors: Blaine D. Johs, Lincoln, NE (US); Ping He, Lincoln, NE (US); Galen L. Pfeiffer, Lincoln, NE (US); Steven E. Green, Lincoln, NE (US); Christopher A. Goeden, Lincoln, NE (US); Martin M. Liphardt, Lincoln, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 390 days.

(21) Appl. No.: 11/084,827

(22) Filed: Mar. 21, 2005

Related U.S. Application Data

(60) Provisional application No. 60/611,173, filed on Sep. 17, 2004.

(51) Int. Cl.
*G01J 4/00* (2006.01)
(52) U.S. Cl. .................................................. 356/364
(58) Field of Classification Search ............... None
See application file for complete search history.

(56) References Cited

U.S. PATENT DOCUMENTS

| | | | | |
|---|---|---|---|---|
| 4,139,263 | A | * | 2/1979 | Lehureau et al. ........... 359/494 |
| 4,210,401 | A | | 7/1980 | Batten ........................ 356/369 |
| 4,332,476 | A | | 6/1982 | Stenberg et al. ............. 356/369 |
| 4,790,659 | A | | 12/1988 | Erman et al. ................ 356/369 |
| 5,229,833 | A | | 7/1993 | Stewart ....................... 356/364 |
| 5,963,327 | A | | 10/1999 | He et al. ..................... 356/369 |
| 5,969,818 | A | * | 10/1999 | Johs et al. ................... 356/369 |
| RE38,153 | E | | 6/2003 | Finarov ....................... 356/630 |
| 6,714,301 | B2 | | 3/2004 | Otsuki et al. ................ 356/369 |
| 6,795,184 | B1 | | 9/2004 | Herzinger et al. .......... 356/369 |
| 2002/0159063 | A1 | | 10/2002 | Kanzaki | |
| 2004/0085538 | A1 | | 5/2004 | Hovinen et al. | |

* cited by examiner

*Primary Examiner*—Tu T Nguyen
(74) *Attorney, Agent, or Firm*—James D. Welch

(57) ABSTRACT

A system for stabilizing the angle of incidence a beam of electromagnetic radiation from a vertically oriented Arc lamp onto a horizontally oriented sample surface.

12 Claims, 2 Drawing Sheets

CONTROL OF UNCERTAIN ANGLE OF INCIDENCE OF BEAM FROM ARC LAMP

This Application Claims benefit of Provisional Application Ser. No. 60/611,173 Filed Sep. 17, 2004.

TECHNICAL FIELD

The disclosed invention relates to the application of Arc Lamps, and more particularly to a system for maintaining consistency of an oblique angle of incidence a beam of electromagnetic radiation therefrom onto a horizontally oriented sample, as the lamp ages.

BACKGROUND

Arc Lamps comprise electrodes which are separated by a distance in a sealed volume in which is contained a gas which, when energized, emits electromagnetic radiation typically comprising a spectrum of wavelengths. The effective origin point of the beam is, of course, located between said electrodes, and said effective origin point can vary over time. Where such an Arc Lamp is utilized to direct a beam of electromagnetic radiation at a sample surface at an oblique angle, the precise measure of said oblique angle can vary with the origin point of the beam, and, as the Arc Lamp ages, the origin point of the beam can vary in position between the electrodes.

With the present invention in mind, a Search of Patents was conducted. As the present invention is a system which comprises a plurality of reflecting means which rotate a "vertically" oriented beam into a "horizontally" oriented beam in ellipsometer and the like systems, the Search was focused on ellipsometer and the like systems which comprise a plurality of reflective means.

The following Patents all describe ellipsometer or the like systems which comprise a plurality of reflective means:
  U.S. Pat. No. RE38,253 to Finarov;
  U.S. Pat. No. 6,714,301 to otsuki et al.;
  U.S. Pat. No. 6,753,962 to Opsal et al.;
  U.S. Pat. No. 5,229,833 to Stewart;
  U.S. Pat. No. 4,790,659 to Erman et al.;
  U.S. Pat. No. 4,210,401 to Batten;
  U.S. Pat. No. 5,963,327 to He et al.;
  U.S. Pat. No. 6,795,184 to Herzinger et al.
  U.S. Pat. No. 4,681,450 to Azzam;
  U.S. Pat. No. 4,332,476 to Stenberg et al.
  Published Application No. US 2004/0085538 A1 by Hovinen et al.;
  Published Application No. US 2002/0159063 A1 by Kanzaki.

While many references describe causing a beam of electromagnetic radiation to undergo a plurality of reflections in ellipsometer or the like systems, none suggest utilizing a plurality of reflecting means to rotate the locus of an Arc lamp arc from substantially vertical to substantially horizontal, in order to prevent lamp aging from changing the effective angle-of-incidence of a beam of electromagentic radiation produced by said Arc lamp, with respect to a sample surface.

DISCLOSURE OF THE INVENTION

In broad terms, the present invention comprises a system for rotating an electromagnetic radiation source image which is elongated in a first plane into an elongated source image oriented substantially 90 degrees with respect thereto. In more detail, the present invention is a system which comprises at least first and second reflecting means which are oriented with respect to one another so as to reflect an incident elongated image in a source plane of incidence, orthogonally into a plane which is rotated substantially ninety (90) degrees thereto.

In more detail yet, the disclosed invention can be described as a system for providing an essentially constant Angle-of-Incidence from a vertically ("Y" axis) oriented Arc Lamp (which comprises electrodes which are separated by some distance in said "Y" dimension in a sealed volume in which is contained a gas which when energized emits a beam of electromagnetic radiation), to a sample surface in the "X"-"Z" plane even when the effective origin point of said beam varies in location between said electrodes. Said system comprises:
  a) a first reflecting means; and
  b) a second reflecting means.

Said first reflecting means is positioned to receive an "X" axis directed beam of electromagnetic radiation from said Arc lamp and reflect it essentially 90 degrees into a "Y" axis directed beam toward said second reflecting means. Said second reflecting means is oriented to reflectively direct said received "Y" axis directed beam, into a "Y"-"Z" Plane locus and onto said sample surface at an oblique Angle-of-Incidence.

It is to be understood that the use of the terminology "X" "Y" and "Z" to identify axes are to be understood to identify mutually perpendicular directions in a system frame of reference. The described system can be rotated around at least one arbitrary laboratory frame or reference axis without the relative positioning of said Arc Lamp and said first and second reflecting means being altered. That is the system will still function even though its "X" "Y" and "Z" axes are offset from the "X" "Y" and "Z" axes of a laboratory in which the system is present, and aligned orientation with a laboratory frame of reference is not limiting.

The first and second reflecting means can be mirrors or prisms or any functional means for reflecting an electromagnetic beam as describe.

An application of the present invention provides that the system comprise a source of electromagnetic-radiation which presents an elongated image in a first plane, a polarizer, a stage for supporting a sample, an analyzer and a detector, said system optionally comprising at least one compensator between said polarizer and analyzer, said system being characterized by the presence of a means for rotating said electromagnetic radiation source image which is elongated in a first plane into an elongated source image oriented in a second plane which is substantially 90 degrees with respect thereto. While not limiting, said first plane can be substantially vertical in a laboratory frame of reference, and said second plane is oriented substantially horizontally. Further, said means for rotating said electromagnetic radiation source image which is elongated in a first plane into an elongated source image oriented in a second plane which is substantially 90 degrees with respect thereto comprises at least first and second reflecting means, at least one of said reflecting means being oriented to reflect an incident elongated source image substantially ninety (90) degrees.

Specifically, the present invention is a system such as a reflectometer, spectrophotometer, ellipsometer, polarimeter or the like comprising an arc lamp for providing a beam of electromagnetic radiation, a stage for supporting a sample, and a detector of electromagentic radiation;

said system, between said arc lamp and said stage, further comprising;
  a first reflecting means; and
  a second reflecting means;
  said first reflecting means being positioned to receive an "X" axis directed beam of electromagnetic radiation from said Source and reflect it 90 degrees into a "Y" axis directed beam toward said second reflecting means, and
  said second reflecting means being oriented to reflectively direct said beam in a "Y"-"Z" Plane locus and onto said sample surface at an oblique Angle-of-Incidence.

Said system can comprise a polarizer between said arc lamp and said stage, and an analyzer between said stage and said detector, to form an ellipsometer system. And said system can yet further comprise at least one compensator between said arc lamp and said detector to form a polarimeter system.

A method of providing a beam of electromagnetic radiation from a source thereof which provides a variable effective origin point comprising the steps of:

a. providing a system for providing a constant Angle-of-Incidence of a beam of electromagnetic radiation from a vertically oriented Source which provides a variable effective origin point of said beam, said system comprising:
  a first reflecting means; and
  a second reflecting means;

positioning said first and second reflecting means with respect to said Source such that;
  said first reflecting means is positioned to receive an "X" axis directed beam of electromagnetic radiation from said Source and reflect it 90 degrees into a "Y" axis directed beam toward said second reflecting means, and
  said second reflecting means is oriented to reflectively direct said beam in a "Y"-"Z" Plane locus and onto said sample surface at an oblique Angle-of-Incidence;

b. causing said source to emit a beam of electromagnetic radiation, reflect from said first and second reflecting means and then impinge upon said sample surface at a constant Angle-of-Incidence regardless of the "Y" axis location of the effective source point of a beam of electromagnetic radiation emitted thereby toward said first reflective means.

The present invention will be better understood by reference to the Detailed Description Section of this Specification, in conjunction with the Drawings.

SUMMARY OF THE INVENTION

It is therefore a purpose and/or summary of the present invention to teach a system for rotating the orientation of an arc in an arc lamp 90 degrees.

It is yet another purpose and/or summary of the present invention to teach application of a system for rotating the orientation of an arc in an arc lamp 90 degrees in reflectometer, spectrophotometer, ellipsometer, polarimeter or the like systems.

It is still yet another purpose and/or summary of the present invention to teach a system for rotating an electromagnetic radiation source image which is elongated in a first plane into an elongated source image oriented substantially 90 degrees with respect thereto, comprising at least first and second reflecting means, oriented with respect to another so as to reflect an incident elongated image in a source plane of incidence, orthogonally into a plane at substantially ninety (90) degrees.

It is another purpose and/or summary of the present invention to teach a system for rotating the orientation of an arc in an arc lamp 90 degrees using two reflective means which are oriented with respect to one another such that a beam approaching the first thereof along in an "X" axis direction will be reflected in a "Y" direction by said first reflective means, and such that the resulting "Y" directed reflected beam is directed in a "Y"-"Z" plane direction by reflection from the second of said reflective means.

Other purposes and/or summaries will become apparent upon a reading of the Specification and Claims.

BRIEF DESCRIPTION OF THE DRAWINGS

FIG. 2b shows a perspective view of the system of the present invention shown in FIG. 2a.

DETAILED DESCRIPTION

Figure 1:
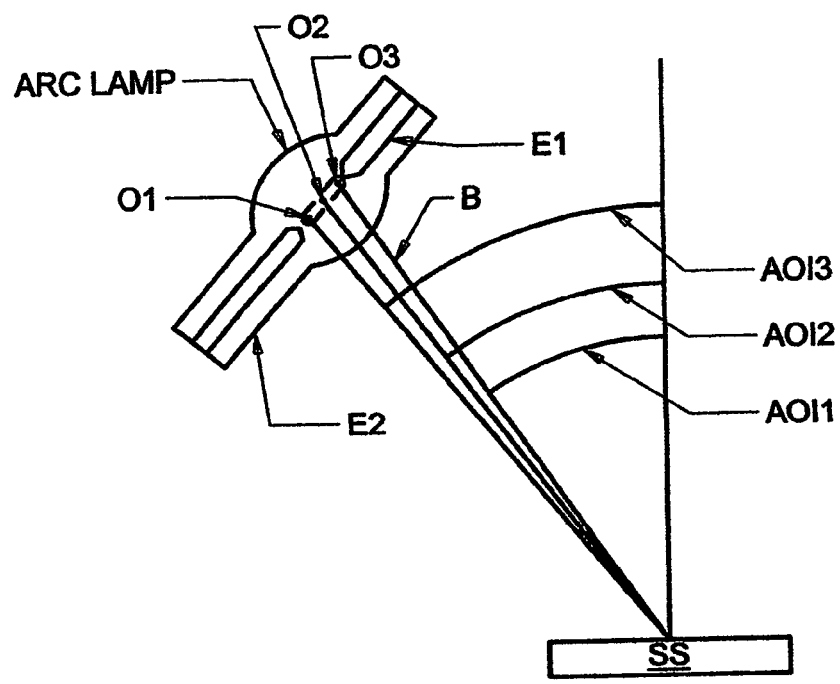
FIG. 1 demonstrates existing art wherein a substantially vertically oriented Arc Lamp is oriented to provide a beam of electromagnetic radiation directly to a sample.

Turning now to the Drawings, there is shown in FIG. 1 an Arc Lamp oriented to provide a beam of electromagnetic radiation directly at a sample. Note that if the effective origin point of the beam (B) between the Electrodes (E1) and (E2) changes, (eg. "O1", "O2", "O3"), so does the Angle-of-Incidence of said beam with respect to the sample surface. This is not acceptable in, for instance, very precise Ellipsometry.

Figure 2A:
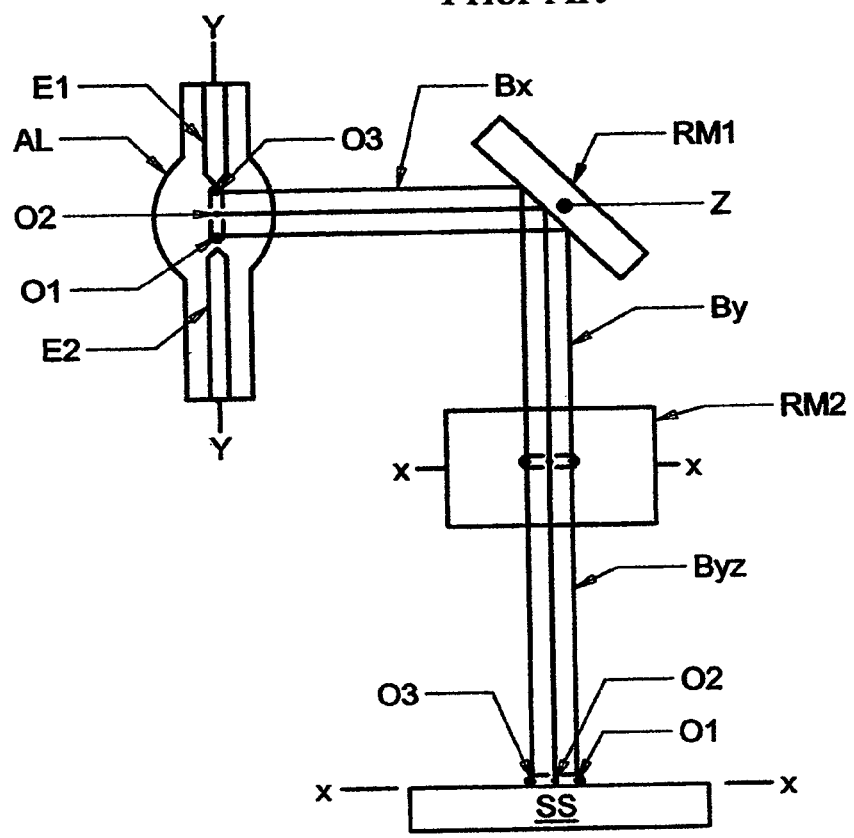
FIG. 2a shows an elevational view of the system of the present invention wherein a substantially vertically oriented Arc Lamp is provides a beam of electromagnetic radiation to a sample via two arc locus orientation rotating reflections.
Figure 2B:
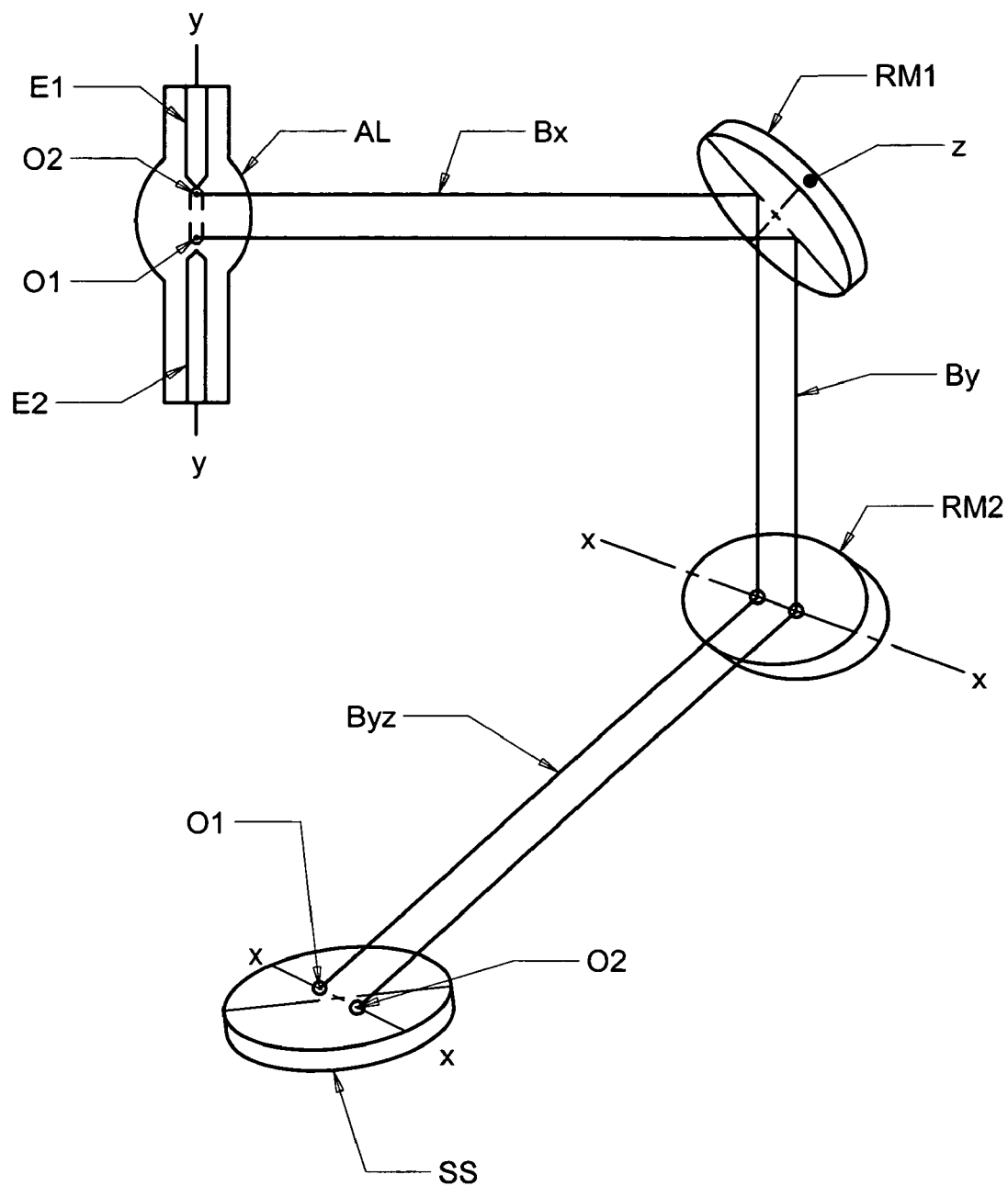

FIG. 2a shows the present invention system. Note that the Arc Lamp is oriented vertically ("Y") axis, and has electrodes (E1) and (E2) separated by a vertically oriented distance. As presented in discussion of FIG. 1, the effective origin, (eg. "O1", "O2", O3"), of the beam (BX) can vary as the Arc Lamp ages. The present invention however, provides a first Reflective Means (RM1) which directs beam (BX) ninety (90) degrees into a downward "Y" axis direction as beam (BY). Beam (BY) then encounters the Second Reflective Means (RM2) which reflects the beam generally downward into the "Y"-"Z" Plane as beam "BYZ", such that it impinges onto Sample (SS). Importantly, note that the orientation of effective origin points "O1", "O2", O3" on the Sample (SS) is altered as compared to the orientation of effective origin points "O1", "O2", O3" at the Arc Lamp, so that no matter the effective origin, the Beam (BZ) Reflected from Reflective Means (RM2) is at a constant oblique angle to the Sample surface, in the "Y"-"Z" Plane as beam "BYZ". It should be appreciated that the First Reflective Means (RM1) is oriented by rotation about a "Z"-axis pivot, and that Second Reflective Means (RM2) is rotated about an "X"-axis pivot. Preferred practice provides that both the First Reflective Means (RM1) be rotated about the "Z" axis so that the angle of incidence and reflection to and therefrom of the beams "BX" and "BY are 45 degrees. Second Reflective Means (RM2) is rotated so as to provide a desired Angle-of-Incidence of beam "BYZ" with respect to the Sample (SS) surface. FIG. 2b shows a perspective view of the system shown in FIG. 2a, to aid with visualizing the system in three-dimensions.

By causing an image of the Arc Lamp to rotate ninety (90) degrees before it impinges onto the Sample (SS), the problem of a changing Angle-of-Incidence with Arch Lamp aging, as demonstrated in FIG. 1, is eliminated. The beam "BYZ" approaches the Sample (SS) surface at the same Angle-of-Incidence no matter the effective origin point of the beam "BX" which exits the Arc Lamp.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A system for rotating an electromagnetic radiation source image provided by a source having a substantially transmissive exit surface for emitting a spectroscopic beam which is elongated in a first plane, into an elongated source image oriented in a second plane oriented substantially 90 degrees with respect to said first plane, comprising at least first and second reflecting means oriented with respect to one another so as to reflect an incident elongated image in a source plane of incidence, orthogonally into a plane rotated substantially ninety (90) degrees thereto.

2. A system comprising a source of electromagnetic radiation having a substantially transmissive exit surface for emitting a spectroscopic beam which presents an elongated image in a first plane, a polarizer, a stage for supporting a sample, an analyzer and a detector, said system optionally comprising at least one compensator between said polarizer and analyzer;
said system being further characterized by the presence of a means for rotating said electromagnetic radiation source image which is elongated in a first plane into an elongated source image oriented in a second plane which is substantially 90 degrees with respect thereto.

3. A system as in claim 2 in which said first plane is substantially vertical in a laboratory frame of reference, and in which said second plane is oriented substantially horizontal therein.

4. A system as in claim 2 in which said means for rotating said electromagnetic radiation source image which is elongated in a first plane into an elongated source image oriented in a second plane which is substantially 90 degrees with respect thereto comprises at least first and second reflecting means, at least one of said reflecting means being oriented to reflect an incident elongated source image substantially ninety (90) degrees.

5. A system for providing a constant angle-of-incidence from a vertically oriented arc lamp having a substantially transmissive exit surface for emitting a spectroscopic beam, said arc lamp comprising electrodes which are separated by some distance in a sealed volume in which is contained a gas which when energized emits a physically elongated beam of electromagnetic radiation, to a sample surface even when the effective origin point of said beam varies in location between said electrodes, said system comprising:
a) a first reflecting means; and
b) a second reflecting means;
said first reflecting means being positioned to receive an "X" axis directed beam of electromagnetic radiation from said Arc lamp and reflect it substantially 90 degrees into a "Y" axis directed beam toward said second reflecting means,
said second reflecting means being oriented to reflectively direct said beam in a "Y"-"Z" Plane locus and onto said sample surface at an oblique Angle-of-Incidence.

6. A system as in claim 5 which is rotated around at least one axis without the relative positioning of said Arc Lamp and said first and second reflecting means being altered.

7. A system as in claim 5 in which said first reflecting means is a mirror.

8. A system as in claim 5 in which said first reflecting means is a prism.

9. A method of providing a beam of electromagnetic radiation from a source thereof having a substantially transmissive exit surface for emitting a spectroscopic beam and which provides a variable effective beam origin point comprising the steps of:
a. providing a system for providing a constant angle-of-incidence of a beam of electromagnetic radiation from a vertically oriented source which provides a variable effective origin point of said beam, said system comprising:
a first reflecting means; and
a second reflecting means;
positioning said first and second reflecting means with respect to said Source such that;
said first reflecting means is positioned to receive an "X" axis directed beam of electromagnetic radiation from said Source and reflect it 90 degrees into a "Y" axis directed beam toward said second reflecting means, and
said second reflecting means is oriented to reflectively direct said beam in a "Y"-"Z" Plane locus and onto said sample surface at an oblique Angle-of-Incidence;
b. causing said source to emit a beam of electromagnetic radiation via said substantially transmissive exit surface for emitting a spectroscopic beam, reflect from said first and second reflecting means and then impinge upon said sample surface at a constant Angle-of-Incidence regardless of the "Y" axis location of the effective source point of a beam of electromagnetic radiation emitted thereby toward said first reflective means.

10. A system such as a reflectometer, spectrophotometer, ellipsometer, polarimeter or the like comprising an arc lamp having a substantially transmissive exit surface for emitting a spectroscopic beam of electromagnetic radiation, a stage for supporting a sample, and a detector of electromagentic radiation;
said system, between said arc lamp and said stage, further comprising;
a first reflecting means; and
a second reflecting means;
said first reflecting means being positioned to receive an "X" axis directed beam of electromagnetic radiation from said Source and reflect it 90 degrees into a "Y" axis directed beam toward said second reflecting means, and
said second reflecting means being oriented to reflectively direct said beam in a "Y"-"Z" Plane locus and onto said sample surface at an oblique Angle-of-Incidence.

11. A system as in claim 10, which comprises a polarizer between said arc lamp and said stage, and an analyzer between said stage and said detector.

12. A system as in claim 11, which comprises at least one compensator between said arc lamp and said detector.

* * * * *